(12) United States Patent
Smits et al.

(10) Patent No.: US 11,457,584 B2
(45) Date of Patent: Oct. 4, 2022

(54) LETTUCE VARIETY 79-941 RZ

(71) Applicant: RIJK ZWAAN ZAADTEELT EN ZAADHANDEL B.V., De Lier (NL)

(72) Inventors: Egbert Carolus Johannes Smits, De Lier (NL); Clément Michel Bernard Morice, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 17/090,972

(22) Filed: Nov. 6, 2020

(65) Prior Publication Data
US 2021/0137043 A1   May 13, 2021

Related U.S. Application Data

(60) Provisional application No. 62/932,535, filed on Nov. 8, 2019.

(51) Int. Cl.
*A01H 5/10* (2018.01)
*A01H 6/14* (2018.01)

(52) U.S. Cl.
CPC .......... *A01H 6/1472* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 7,371,930 B1 | 5/2008 | Knerr | |
| 9,161,510 B2 | 10/2015 | Ammerlaan | |
| 9,326,479 B2 | 5/2016 | Roosenboom-Kooijman | |
| 9,554,550 B2 | 1/2017 | Roosenboom-Kooijmans | |
| 10,321,651 B2 | 6/2019 | Roosenboom-Kooijmans et al. | |
| 10,426,117 B2 | 10/2019 | Luijten | |
| 10,492,407 B2 | 12/2019 | Tomas Garcia et al. | |
| 2019/0037790 A1 | 2/2019 | Morice | |
| 2019/0141932 A1 | 5/2019 | Roosenboom-Kooijmans et al. | |
| 2019/0141933 A1 | 5/2019 | Roosenboom-Kooijmans et al. | |
| 2019/0191653 A1 | 6/2019 | Roosenboom-Kooijmans et al. | |
| 2019/0191654 A1* | 6/2019 | Morice | A01H 5/12 |

OTHER PUBLICATIONS

IBEB press release New race of Bremia lactucae 81:27 identified and nominated, May 2010; Plantum NL, Postbus 462, 2800 AL GOUDA.

Michelmore R. & Ochoa. O. Breeding Crisphead Lettuce. In: California Lettuce Research Board, Annual Report 2005-2006, 2006, Satinas, California, pp. 55-68.

Schettini, T.M., Legg, E.J., Michelmore, R.W., 1991. Insensitivity to metalaxyl in California populations of Bremia lactucae and resistance of California lettuce cultivars to Downy Mildew, Disease Control and Pest Management, pp. 64-70.

(Continued)

*Primary Examiner* — Matthew R Keogh
*Assistant Examiner* — David R Byrnes
(74) *Attorney, Agent, or Firm* — Duane Morris LLP; Thomas J. Kowalski; Deborah L. Lu

(57) ABSTRACT

The present invention relates to a *Lactuca sativa* seed designated 79-941 RZ. The present invention also relates to a *Lactuca sativa* plant produced by growing the 79-941 RZ seed. The invention further relates to methods for producing the lettuce cultivar, represented by lettuce variety 79-941 RZ.

24 Claims, 2 Drawing Sheets
(2 of 2 Drawing Sheet(s) Filed in Color)

(56) References Cited

OTHER PUBLICATIONS

Van Ettekoven, K. et al., Identification and denomination of 'new' races of Bremia lactucae, In: Lebeda, A. and Kristkova, E (eds.), Eucarpia Leafy Vegetables, 1999.
Van der Arend et al. Identification and denomination of "new" races of Bremia lactucae in Europe by IBEB until 2002. In: Van Hintum, Th et al. (eds.), Eucarpia Leafy Vegetables.
Cortazar RZ (41-233) Rijk Zwaan AU (Oct. 22, 2019).
Lettuce: Lettuce Resources, Rijk Zwaan AU 2019 (Oct. 22, 2019).
Lalique RZ 44-17—Rijk Zwaan USA and Canada (2018).

* cited by examiner

LETTUCE VARIETY 79-941 RZ

INCORPORATION BY REFERENCE

This application claims priority to U.S. provisional patent application Ser. No. 62/932,535 filed 8 Nov. 2019.

The foregoing applications, and all documents cited therein or during their prosecution ("appin cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new lettuce (*Lactuca sativa*) variety designated 79-941 RZ. Lettuce variety 79-941 RZ exhibits a combination of traits including resistance to downy mildew (*Bremia lactucae*) races B1:16EU to B1:36EU and B1:1US to B1:9US, resistance to currant-lettuce aphid (*Nasonovia ribisnigri*) biotype Nr:0, and resistance to Lettuce Mosaic Virus (LMV) race LMV:1, as well as having a reduced wound induced surface discoloration and a medium plant size.

BACKGROUND OF THE INVENTION

All cultivated forms of lettuce belong to the highly polymorphic species, *Lactuca sativa*, which is grown for its edible head and leaves. As a crop, lettuces are grown commercially wherever environmental conditions permit the production of an economically viable yield.

*Lactuca sativa* is in the Cichoreae tribe of the Asteraceae (Compositae) family. Lettuce is related to chicory, sunflower, aster, scorzonera, dandelion, artichoke and chrysanthemum. Sativa is one of about 300 species in the genus *Lactuca*.

Lettuce cultivars are susceptible to a number of pests and diseases such as downy mildew (*Bremia lactucae*). Every year this disease leads to millions of dollars of lost lettuce crop throughout the world. Downy mildew (*Bremia lactucae*) is highly destructive on lettuce grown at relatively low temperature and high humidity. Downy mildew is caused by a fungus, *Bremia lactucae*, which can be one of the following strains: B1:16EU, B1:17EU, B1:18EU, B1:20EU, B1:21EU, B1:22EU, B1:23EU, B1:24EU, B1:25EU, B1:26EU, B1:27EU, B1:29EU, B1:30EU, B1:31EU, B1:32EU, B1:33EU, B1:34EU, B1:35EU, B1:36EU (Van Ettekoven, K. et al., "Identification and denomination of 'new' races of *Bremia lactucae*," In: Lebeda, A. and Kristkova, E (eds.), Eucarpia Leafy Vegetables, 1999, Palacky University, Olomouc, Czech Republic, pp. 171-175; Van der Arend et al. "Identification and denomination of "new" races of *Bremia lactucae* in Europe by IBEB until 2002." In: Van Hintum, Th et al. (eds.), Eucarpia Leafy Vegetables Conference 2003, Centre for Genetic Resources, Wageningen, The Netherlands, p. 151; Plantum N L (Dutch association for breeding, tissue culture, production and trade of seeds and young plants), Van der Arend et al. "Identification and denomination of "new" races of *Bremia lactucae* in Europe by IBEB until 2002." In: Van Hintum, Th et al. (eds.), Eucarpia Leafy Vegetables Conference 2003, Centre for Genetic Resources, Wageningen, The Netherlands, p. 151; Plantum N L (Dutch association for breeding, tissue culture, production and trade of seeds and young plants); IBEB press release "New race of *Bremia lactucae* B1:27 identified and nominated", May 2010; Plantum N L (Dutch association for breeding, tissue culture, production and trade of seeds and young plants), IBEB press release, "New races of *Bremia lactucae*, B1:29, B1:30 and B1:31 identified and nominated", August 2013; Plantum N L (Dutch association for breeding, tissue culture, production and trade of seeds and young plants), IBEB press release, "A new race of *Bremia lactucae*, B1:32 identified and nominated in Europe", May 2015), Plantum N L (Dutch association for breeding, tissue culture, production and trade of seeds and young plants), IBEB-EU press release, "A new race of *Bremia lactucae*, B1:33EU identified and denominated in Europe", May 2017; Plantum N L (Dutch association for breeding, tissue culture, production and trade of seeds and young plants), IBEB-EU press release, "Two new races of *Bremia lactucae*, B1:34EU and B1:35EU identified and nominated in Europe", July 2018; Plantum N L (Dutch association for breeding, tissue culture, production and trade of seeds and young plants), IBEB-EU press release, "A new race of *Bremia lactucae*, B1:36EU identified and denominated in Europe", July 2019), B1:1US, B1:2US, B1:3US, B1:4US, B1:5US, B1:6US, B1:7US, B1:8US, B1:9US (Schettini, T. M., Legg, E. J., Michelmore, R. W., 1991. Insensitivity to metalaxyl in California populations of *Bremia lactucae* and resistance of California lettuce cultivars to downy mildew. Phytopathology 81(1). p. 64-70; Michelmore R. & Ochoa. O. "Breeding Crisphead Lettuce." In: California Lettuce Research Board, Annual Report 2005-2006, 2006, Salinas, Calif., pp. 55-68; http://bremia.ucdavis.edu/dataB1_9US.pdf).

Downy mildew causes pale, angular, yellow areas bounded by veins on the upper leaf surfaces. Sporulation occurs on the opposite surface of the leaves. The lesions eventually turn brown, and they may enlarge and coalesce. These symptoms typically occur first on the lower leaves of the lettuce, but under ideal conditions may move into the upper leaves of the head. When the fungus progresses to this degree, the head cannot be harvested. Less severe damage requires the removal of more leaves than usual, especially when the lettuce reaches its final destination.

Of the various species of aphids that feed on lettuce, the currant-lettuce aphid (*Nasonovia ribisnigri*) is the most destructive species because it feeds both on the leaves of the lettuce as well as the heart of the lettuce, making it difficult to control with conventional insecticides. The lettuce aphid feeds by sucking sap from the lettuce leaves. Although direct damage to the lettuce may be limited, its infestation has serious consequences because the presence of aphids makes lettuce unacceptable to consumers.

Lettuce mosaic virus (LMV) mainly infects lettuce seeds, which is the primary way that the virus is introduced to lettuce in the fields, but also can infect numerous crops and weeds, thereby creating reservoirs of the virus. LMV also can be vectored by aphids, which spread the virus within a lettuce field and introduce it into lettuce fields from infected weeds and crops outside the field.

Symptoms of LMV vary greatly. Leaves of plants that are infected at a young stage are stunted, deformed and (in some varieties) show a mosaic or mottling pattern. Such plants rarely grow to full size; head lettuce varieties infected early fail to form heads. Plants that are infected later in the growth cycle show a different set of symptoms. These plants may reach full size, but the older outer leaves turn yellow, twisted, and otherwise are deformed. On head lettuce, the wrapper leaves often will curve back away from the head and developing heads may be deformed. In some cases, brown necrotic flecks occur on the wrapper leaves.

The production of packaged salad mixes, for example, involves harvesting and processing of lettuce, which induces a strong wound response on the cut surfaces. Such a wound-induced response can lead to a rapid deterioration of the processed product. This deterioration is manifested as a brown or pink discoloration at, or adjacent to the wound surface. The brown or pink color that develops over time on the cut leaf surface makes the product highly unattractive to potential customers.

The wound-induced surface discoloration can in part be countered by reducing oxygen levels in the packaging. However, using specialized packaging is costly and may result in anaerobic conditions. Anaerobic conditions may reduce shelf life and may promote the growth of microorganisms that produce a bad smell, reducing the overall attractiveness and taste of the product. Therefore lettuce plants that exhibit reduced wound-induced discoloration of cut leaf surfaces is desirable. Such lettuce plants stay visually more attractive post-processing, and the need for reduced oxygen levels in the packaging of the cut leaves of these lettuce plants is minimized.

Citation or identification of any document in this application is not an admission that such document is available as prior art to the present invention.

SUMMARY OF THE INVENTION

Given the need expressed by relevant stakeholders for a lettuce variety which is resistant to downy mildew (*Bremia lactucae*) races Bl:16EU to Bl:36EU and Bl:1US to Bl:9US, resistant to currant-lettuce aphid (*Nasonovia ribisnigri*) biotype Nr:0, and resistant to Lettuce Mosaic Virus (LMV) race LMV:1, as well as having a reduced wound induced surface discoloration and a medium plant size. the present invention addresses this need by providing a new type of lettuce (*Lactuca sativa*) variety, designated 79-941 RZ.

The present invention provides a new lettuce (*Lactuca sativa*) variety designated 79-941 RZ. This new lettuce variety exhibits a combination of traits including resistance to downy mildew (*Bremia lactucae*) races Bl:16EU to Bl:36EU and Bl:1US to Bl:9US, resistance to currant-lettuce aphid (*Nasonovia ribisnigri*) biotype Nr:0, and resistance to Lettuce Mosaic Virus (LMV) race LMV:1, as well as having a reduced wound induced surface discoloration and a medium plant size.

The present invention provides seed of a lettuce (*Lactuca sativa*) variety designated 79-941 RZ. A sample of seeds of said lettuce variety, have been deposited with the National Collections of Industrial, Marine and Food Bacteria (NCIMB) in Bucksburn, Aberdeen AB21 9YA, Scotland, UK and have been assigned NCIMB Accession No. 43672.

In one embodiment, the invention provides a lettuce plant grown from the seed of lettuce (*Lactuca sativa*) variety 79-941 RZ.

In another embodiment, the invention provides a lettuce plant designated 79-941 RZ, which is a plant grown from seed having been deposited under NCIMB Accession No. 43672.

In one embodiment, the invention provides for a lettuce plant which may comprise genetic information for exhibiting all of the physiological and morphological characteristics of a plant of the invention, wherein the genetic information is as contained in a plant, a sample of seed of said variety having been deposited under NCIMB Accession No. 43672.

In one embodiment, the invention provides for a lettuce plant exhibiting all the physiological and morphological characteristics of a plant of the invention, and having the genetic information for so exhibiting the combination of traits, wherein the genetic information is as contained in a plant, a sample of seed of said variety having been deposited under NCIMB Accession No. 43672.

In an embodiment of the present invention, there also is provided parts of a lettuce plant of the invention, which may include parts of a lettuce plant exhibiting all the physiological and morphological characteristics of a plant of the invention, or parts of a lettuce plant having any of the mentioned resistance(s) and a combination of traits including one or more or all morphological and physiological characteristics tabulated herein, including parts of lettuce variety 79-941 RZ, wherein the plant parts are involved in sexual reproduction, which include, without limitation, microspores, pollen, ovaries, ovules, embryo sacs or egg cells and/or wherein the plant parts are suitable for vegetative reproduction, which include, without limitation, cuttings, roots, stems, cells or protoplasts and/or wherein the plant parts are tissue culture of regenerable cells in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems. The plants of the invention from which such parts may come from include those wherein a sample of seed of which having been deposited under NCIMB Accession No. 43672 or lettuce variety or cultivar designated 79-941 RZ, as well as seed from such a plant, plant parts of such a plant (such as those mentioned herein) and plants from such seed and/or progeny of such a plant, advantageously progeny exhibiting such combination of such traits, each of which, is within the scope of the invention; and such combination of traits.

In a further embodiment there is a plant regenerated from the above-described plant parts or regenerated from the above-described tissue culture. Advantageously such a plant may have morphological and/or physiological characteristics of lettuce variety 79-941 RZ and/or of a plant grown from seed, a sample of seed of which having been deposited under NCIMB Accession No. 43672—including without limitation such plants having all of the physiological and morphological characteristics of lettuce variety 79-941 RZ and/or of a plant grown from seed, a sample of seed of which having been deposited under NCIMB Accession No. 43672.

Accordingly, in still a further embodiment, there is provided a lettuce plant having all of the physiological and morphological characteristics of lettuce variety 79-941 RZ, a sample of seed of which having been deposited under NCIMB Accession No. 43672. Such a plant may be grown from the seeds, regenerated from the above-described plant parts, or regenerated from the above-described tissue culture. A lettuce plant having any of the aforementioned resistance(s), and one or more morphological or physiological characteristics recited or tabulated herein, and a lettuce plant advantageously having all of the aforementioned resistances and the characteristics recited and tabulated herein, are preferred. Parts of such plants—such as those plant parts above-mentioned—are encompassed by the invention.

In a further aspect, the invention provides a method of vegetatively propagating a plant of lettuce variety 79-941 RZ which may comprise (a) collecting tissue capable of being propagated from a plant of lettuce 79-941 RZ, a sample of seed of said variety having been deposited under NCIMB accession No. 43672 and (b) cultivating the tissue to obtain proliferated shoots and rooting the proliferated shoots to obtain rooted plantlets. Optionally the invention further may comprise growing plants from the rooted plantlets. Plantlets and plants produced by these methods, are encompassed by the invention.

In one embodiment, there is provided a method for producing a progeny of lettuce cultivar 79-941 RZ which may comprise crossing a plant designated 79-941 RZ with itself or with another lettuce plant, harvesting the resultant seed, and growing said seed.

In a further embodiment, a progeny plant is provided which is produced by this method, wherein said progeny exhibits a combination of traits including resistance to downy mildew (*Bremia lactucae*) races Bl:16EU to Bl:36EU and Bl:1US to Bl:9US, resistance to currant-lettuce aphid (*Nasonovia ribisnigri*) biotype Nr:0, and resistance to Lettuce Mosaic Virus (LMV) race LMV:1, as well as having a reduced wound induced surface discoloration and a medium plant size.

In another embodiment, a progeny plant is provided which is produced by the above method, wherein said progeny exhibits all the morphological and physiological characteristics of the lettuce variety designated 79-941 RZ, a sample of seed of said variety having been deposited under NCIMB accession No. 43672.

In a further embodiment there is provided a progeny plant produced by sexual or vegetative reproduction, grown from seeds, regenerated from the above-described plant parts, or regenerated from the above-described tissue culture of the lettuce cultivar or a progeny plant thereof, a sample of seed of which having been deposited under NCIMB Accession No. 43672. The progeny may have any of the aforementioned resistance(s), and one or more morphological or physiological characteristics recited or tabulated herein, and a progeny plant advantageously having all of the aforementioned resistances and the characteristics recited and tabulated herein, are preferred.

Progeny of the lettuce variety 79-941 RZ may be modified in one or more other characteristics, in which the modification is a result of, for example and without limitation, mutagenesis or transformation with a transgene.

In still another embodiment, the present invention provides progeny of lettuce cultivar 79-941 RZ produced by sexual or vegetative reproduction, grown from seed, regenerated from the above-described plant parts, or regenerated from the above-described tissue culture of the lettuce cultivar or a progeny plant thereof.

The invention further relates to a method for producing a seed of a 79-941 RZ-derived lettuce plant which may comprise (a) crossing a plant of lettuce variety 79-941 RZ, a sample of seed of which having been deposited under NCIMB Accession No. 43672, with a second lettuce plant, and (b) whereby seed of a 79-941 RZ-derived lettuce plant forms. This method may further comprise (c) crossing a plant grown from 79-941 RZ-derived lettuce seed with itself or with a second lettuce plant to yield additional 79-941 RZ-derived lettuce seed, (d) growing the additional 79-941 RZ-derived lettuce seed of step (c) to yield additional 79-941 RZ-derived lettuce plants, and (e) repeating the crossing and growing of steps (c) and (d) for an additional 3-10 generations to generate further 79-941 RZ-derived lettuce plants, and (f) whereby seed of a 79-941 RZ-derived lettuce plant forms. A seed produced by this method and a plant grown from said seed also form part of the invention.

The invention also relates to a method of introducing at least one new trait into a plant of lettuce variety 79-941 RZ which may comprise: (a) crossing a plant of lettuce variety 79-941 RZ, a sample of seed of which having been deposited under NCIMB Accession No. 43672, with a second lettuce plant that may comprise at least one new trait to produce progeny seed, (b) harvesting and planting the progeny seed to produce at least one progeny plant of a subsequent generation, wherein the progeny plant may comprise the at least one new trait, (c) crossing the progeny plant with a plant of lettuce variety 79-941 RZ to produce backcross progeny seed, (d) harvesting and planting the backcross progeny seed to produce a backcross progeny plant, and (e) repeating steps (c) and (d) for at least three additional generations to produce a lettuce plant of variety 79-941 RZ which may comprise at least one new trait and all of the physiological and morphological characteristics of a plant of lettuce variety 79-941 RZ, when grown in the same environmental conditions. A lettuce plant produced by this method also forms part of the invention.

Mutations can be introduced randomly by means of one or more chemical compounds, such as ethyl methane sulphonate (EMS), nitrosomethylurea, hydroxylamine, proflavine, N-methly-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast neutron exposure, X-rays, gamma irradiation, and/or by insertion of genetic elements, such as transposons, T-DNA, retroviral elements.

Mutations can also be introduced by more specific, targeted introduction of at least one modification by means of homologous recombination, oligonucleotide-based mutation introduction, zinc-finger nucleases (ZFN), transcription activator-like effector nucleases (TALENs) or Clustered Regularly Interspaced Short Palindromic Repeat (CRISPR) systems.

The invention further relates to a method of producing a plant of lettuce variety 79-941 RZ which may comprise at least one new trait, the method which may comprise introducing a mutation or transgene conferring the at least one new trait into a plant of lettuce variety 79-941 RZ, wherein a sample of seed of said variety has been deposited under NCIMB Accession No. 43672. A lettuce plant produced by this method also forms part of the invention.

In still a further embodiment, the invention provides a method of producing a lettuce seed which may comprise crossing a male parent lettuce plant with a female parent lettuce plant and harvesting the resultant lettuce seed, in which the male parent lettuce plant or the female parent lettuce plant is a lettuce plant of the invention, e.g. a lettuce plant having all of the morphological or physiological characteristics tabulated herein, including a lettuce plant of lettuce cultivar 79-941 RZ, a sample of seed of which having been deposited under 43672. The resultant lettuce seed produced by this method and the lettuce plant that is produced by growing said lettuce seed also forms part of the invention.

In still a further embodiment, the invention provides a method of producing a lettuce cultivar which exhibits all of the physiological and morphological characteristics of lettuce variety 79-941 RZ, a sample of seed of said variety having been deposited under NCIMB accession No. 43672.

The invention even further relates to a method of producing lettuce leaves as a food product which may comprise: (a) sowing a seed of lettuce variety 79-941 RZ, a sample of seed of which having been deposited under NCIMB Accession No. 43672, (b) growing said seed into a harvestable lettuce plant and (c) harvesting lettuce leaves or heads from the plant. The invention further comprehends packaging and/or processing the lettuce plants, heads or leaves.

Also encompassed by the invention is a container which may comprise one or more lettuce plants of the invention for harvest of leaves.

Further encompassed by the invention is a method of determining the genotype of a plant of lettuce variety 79-941 RZ, a sample of seed of which has been deposited under NCIMB Accession No. 43672, or a first generation progeny thereof, which may comprise obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms is indicative of lettuce variety 79-941 RZ and/or gives rise to the expression of any one or more, or all, of the physiological and morphological characteristics of lettuce variety 79-941 RZ of the invention.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph), such that Applicants reserve the right and hereby disclose a disclaimer of any previously described product, process of making the product, or method of using the product.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP § 2111.03. In addition, the term "about" is used to indicate that a value includes the standard deviation of error for the device or method being employed to determine the value.

These and other embodiments are disclosed or are obvious from and encompassed by the following Detailed Description.

Deposit

The Deposit with NCIMB Ltd, Ferguson Building, Craibstone Estate, Bucksburn, Aberdeen AB21 9YA, UK, on Oct. 17, 2020, under deposit accession number 43672 was made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawing, in which.

DETAILED DESCRIPTION OF THE INVENTION

Figure 1:
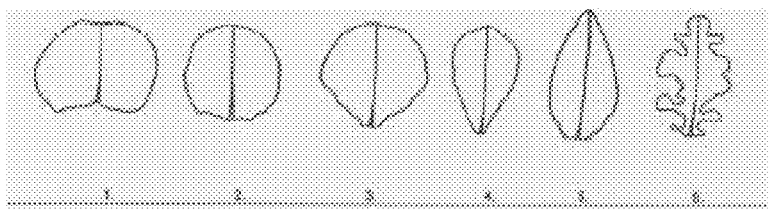
FIG. 1 is an illustration of six different shapes of the fourth leaf from a 20-day old seedling grown under optimal conditions.
Figure 2:
FIG. 2 is a picture of the shape of the fourth leaf of 79-941 RZ.
Figure 3:
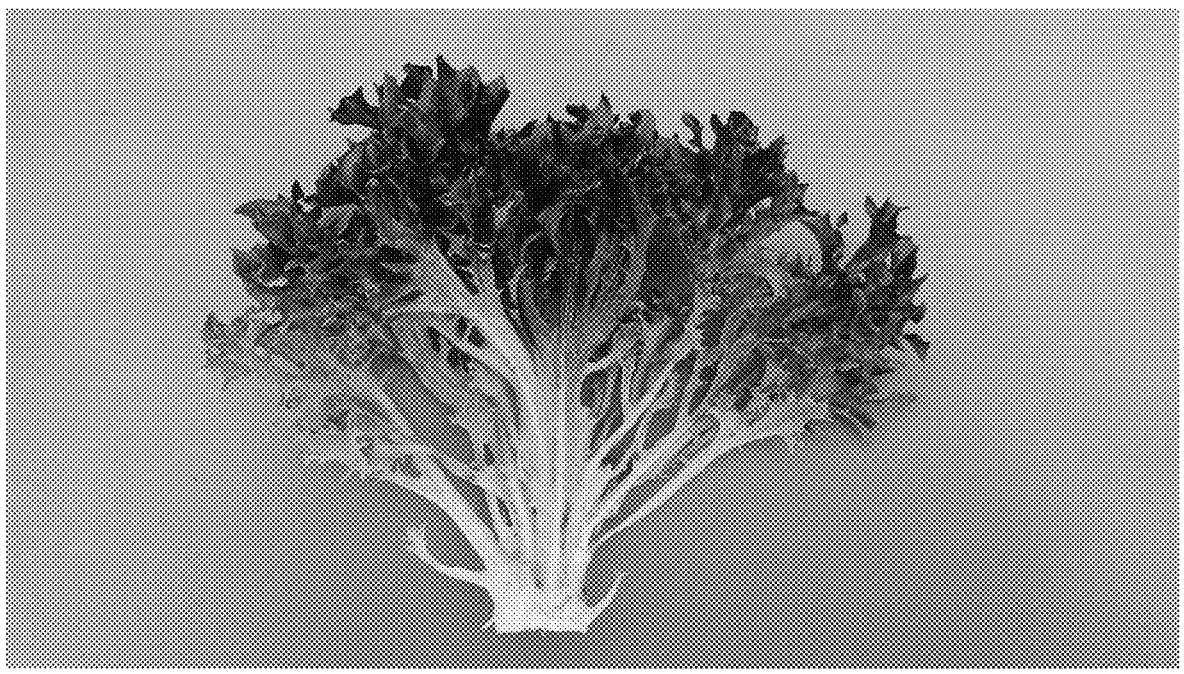
FIG. 3 is a picture of the shape of a mature leaf of 79-941 RZ.

The invention provides methods and compositions relating to plants, seeds and derivatives of a new lettuce variety herein referred to as lettuce variety 79-941 RZ. Lettuce variety 79-941 RZ is a uniform and stable line, distinct from other such lines.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., Principles of Cultivar Development, Volume I, MacMillan Publishing Co., which is hereby incorporated by reference.

When pedigree selection is applied, in general selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes.

Additionally, any breeding method involving selection of plants for the desired phenotype may be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

A detailed description of the development of lettuce variety 79-941 RZ is described in Table 1. The seedlot in year 4, seedlot 18R.8490, was deposited with the NCIMB under deposit number 43672.

TABLE 1

| Year | Description | Location |
| --- | --- | --- |
| 0 | Final F1-cross: plant 14B.254899 × plant 15B.850829 in a glasshouse. | Fijnaart, The Netherlands |
| 1 | F1 plant grown for F2 seed production in glasshouse. | Fijnaart, The Netherlands |
| 2 | F2 plant selected in open field, followed by F3 seed production. | Fijnaart, The Netherlands |
| 2-3 | F3 plant selected in open field, followed by F4 seed production. | Daylesford, Australia |
| 3-4 | F4 plant selected in open field, followed by F5 seed production. | Fijnaart, The Netherlands |
| 4 | F5 line established uniform, multiplied in glasshouse: seedlot 18R.8490 | De Lier, The Netherlands |

In one embodiment, a plant of the invention has all the physiological and morphological characteristics of lettuce variety 79-941 RZ. These characteristics of a lettuce plant of the invention, e.g. variety 79-941 RZ, are summarized in Tables 2 and 3.

Next to the physiological and morphological characteristics mentioned in Tables 2 and 3, a plant of the invention also exhibits resistance to downy mildew (*Bremia lactucae* Regel.) races.

As used herein resistance against *Bremia lactucae* is defined as the ability of a plant to resist infection by each of the various strains B1:16EU to B1:36EU, B1:1US to B1:9US of *Bremia lactucae* Regel. in all stages between the seedling stage and the harvestable plant stage. B1:16EU to B1:36EU means strains B1:16EU, B1:17EU, B1:18EU, B1:20EU, B1:21EU, B1:22EU, B1:23EU, B1:24EU, B1:25EU, B1:26EU, B1:27EU, B1:29EU, B1:30EU, B1:31EU, B1:32EU, B1:33EU, B1:34EU, B1:35EU, B1:36EU (Van Ettekoven K, Van der Arend A J M, 1999. identification and denomination of 'new' races of *Bremia lactucae*. In: Lebeda A, Kristkova E (eds.) Eucarpia leafy vegetables '99. Palacky University, Olomouc, Czech Republic, 1999: 171-175; Van der Arend, A. J. M., Gautier, J., Guenard, M., Michel, H., Moreau, B., de Ruijter, J., Schut, J. W. and de Witte, I. (2003). Identification and denomination of 'new' races of *Bremia lactucae* in Europe by IBEB until 2002. In: Eucarpia leafy vegetables 2003. Proceedings of the Eucarpia Meeting on leafy vegetables genetics and breeding. Noorwijkerhout, The Netherlands. Eds. Van Hintum T., Lebeda A., Pink D., Schut J. pp 151-160; Van der Arend A J M, Gautier J, Grimault V, Kraan P, Van der Laan R, Mazet J, Michel H, Schut J W, Smilde D, De Witte I (2006) Identification and denomination of "new" races of *Bremia lactucae* in Europe by IBEB until 2006; incorporated herein by reference; Plantum N L (Dutch association for breeding, tissue culture, production and trade of seeds and young plants), IBEB press release, "New race of *Bremia lactucae* B1:27 identified and nominated", May 2010; Plantum N L (Dutch association for breeding, tissue culture, production and trade of seeds and young plants), IBEB press release, "New races of *Bremia lactucae*, B1:29, B1:30 and B1:31 identified and nominated", August 2013; Plantum N L (Dutch association for breeding, tissue culture, production and trade of seeds and young plants), IBEB press release, "A new race of *Bremia lactucae*, B1:32 identified and nominated in Europe", May 2015; Plantum N L (Dutch association for breeding, tissue culture, production and trade of seeds and young plants), IBEB-EU press release, "A new race of *Bremia lactucae*, B1:33EU identified and denominated in Europe", May 2017; Plantum N L (Dutch association for breeding, tissue culture, production and trade of seeds and young plants), IBEB-EU press release, "Two new races of *Bremia lactucae*, B1:34EU and B1:35EU identified and nominated in Europe", July 2018; Plantum N L (Dutch association for breeding, tissue culture, production and trade of seeds and young plants), IBEB-EU press release, "A new race of *Bremia lactucae*, B1:36EU identified and denominated in Europe", July 2019). B1:1US to B1:9US means B1:1US, B1:2US, B1:3US, B1:4US, B1:5US, B1:6US, B1:7US, B1:8US, B1:9US (Schettini, T. M., Legg, E. J., Michelmore, R. W., 1991. Insensitivity to metalaxyl in California populations of *Bremia lactucae* and resistance of California lettuce cultivars to downy mildew, Phytopathology 81(1). p.64-'70; Michelmore R. & Ochoa. O. "Breeding Crisphead Lettuce." In: California Lettuce Research Board, Annual Report 2005-2006, 2006, Salinas, Calif., pp. 55-68; http://bremia.ucdavis.edu/data/B1_9US.pdf).

Resistance typically is tested by two interchangeable methods, described by Bonnier, F. J. M. et al. (Euphytica, 61(3):203-211, 1992; incorporated herein by reference). One method involves inoculating 7-day old seedlings, and observing sporulation 10 to 14 days later. The other method involves inoculating leaf discs with a diameter of 18 mm obtained from a non-senescent, fully grown true leaf and observing sporulation 10 days later.

As used herein, resistance against *Nasonovia ribisnigri* (Mosley), or currant-lettuce aphid, is defined as the plant characteristic which results in a non-feeding response of the aphid on the leaves of the plant in all stages between 5 true-leaf stage and harvestable plant stage (U.S. Pat. No. 5,977,443 to Jansen, J. P. A., "Aphid Resistance in Composites," p. 12, 1999; incorporated herein by reference).

Resistance is tested by spreading at least ten aphids of biotype Nr:0 on a plant in a plant stage between 5 true leaves and harvestable stage, and observing the density of the aphid population on the plant as well as the growth reduction after 14 days in a greenhouse, with temperature settings of 23 degrees Celsius in daytime and 21 degrees Celsius at night. Day length is kept at 18 hours by assimilation lights.

As used herein, resistance against lettuce mosaic virus (LMV) may be defined as the ability of the plant to grow normally after LMV infection and to inhibit the virus transmission to seed. Resistance may be tested by mechanical inoculation of young plants in a climate cell or greenhouse, as described by Pink, D. A. C. et al. (Plant Pathology, 41(1): 5-12, 1992), incorporated herein by reference. Inoculated resistant plants grow just as well as uninoculated plants and show no chlorosis or mosaic symptoms. The LMV isolate, which may be used for testing, is Ls-1 (International Union for the Protection of New Varieties of Plants [UPOV], Guidelines for the conduct of tests for distinctness, uniformity and stability; 30 lettuce (*Lactuca sativa* L.), 2002, p. 35; incorporated herein by reference).

As used herein, reduced wound-induced surface discoloration is defined as the ability of a lettuce plant, due to genetic information in its genome, to show a reduced or no discoloration of its wounded surface, as compared to a control lettuce plant of the same type and same color not showing the reduced wound-induced surface discoloration of its wounded surface. For comparison of this trait, the standard variety Codex RZ can be used as a control plant for 79-941 RZ. As used herein, the term "wound" is to mean the irreversible disturbance of the natural plant, tissue and/or cell structure by methods like cutting, punching, slicing, abrasion, squashing, breaking, peeling, crushing, pressing, slashing, grinding, fluid injection, osmotic shock, detaching, mowing, shredding, rubbing and tearing.

This trait can be tested by a leaf disc test in which a round leaf disc is punched from a fresh, fully-grown true leaf of a young plant, for example a plant at the 4-6 true leaf stage. The leaf discs of the plant to be tested and the control plant are incubated between two sheets of wetted filter paper for about 3 to about 7 days at about 5° C. to 7° C. (such as, but not limited to a 3 day incubation at about 5° C.), and the presence or absence of pink discoloration around each leaf disc at the wound surface is observed. A leaf disc taken from a lettuce plant showing a reduced wound-induced surface discoloration trait due to genetic information in its genome which is responsible for the trait, will not show a pink-colored discoloration (or only very faintly) at the edge of the wound surface, and is in any case less than the discoloration of a leaf disc taken from a control lettuce plant, for example a plant of the standard variety Codex R Z, not showing the reduced wound-induced surface discoloration trait which will show pink-colored discoloration at the edge of the wound surface (For leaf disc test, see generally U.S. Pat. No. 8,809,631).

As used herein, the plant size is characterized as being very small, small, medium, large or very large (characteristic 26: Only varieties with Plant: degree of overlapping of upper part of leaves: medium or strong: Head: size, UPOV guidelines TG/13/11). A mature head of 79-941 RZ has a medium size (characteristic 26: 5 medium, UPOV TG/13/11), which is larger than the size of standard variety Codex RZ which has a small to medium size (characteristic 26: 4 small to medium, UPOV TG/13/11), when grown under the same environmental conditions.

Embodiments of the inventions advantageously have one or more, and most advantageously all, of these characteristics.

In Table 2, the seed color, cotyledon shape and characteristics of the fourth leaf of "79-941 RZ" are shown.

TABLE 2

| Character | 79-941 RZ |
|---|---|
| Plant Type | Cutting/Leaf |
| Seed Color | Black |
| Cotyledon Shape | Intermediate |
| Shape of Fourth Leaf | Elongated |
| Cupping of Fourth Leaf | Uncupped |
| Fourth Leaf Apical Margin | Coarsely dentate |
| Fourth Leaf Basal Margin | Coarsely dentate |
| Undulation | Slight |
| Fourth leaf color | Red |
| Anthocyanin distribution | Throughout |
| Anthocyanin concentration | Intense |

In Table 3, the mature leaf and head characteristics of "79-941 RZ" are shown.

TABLE 3

| Character | 79-941 RZ |
|---|---|
| Leaf Color | Red |
| Anthocyanin Distribution | Throughout |
| Anthocyanin concentration | Very intense |
| Margin Incision Depth | Deep |
| Margin Indentation | Shallowly dentate |
| Undulations of the Apical Margin | Strong |
| Leaf Size | Medium |
| Leaf Glossiness | Very glossy |
| Leaf Blistering | Absent/slight |
| Leaf Thickness | Thin |
| Trichomes | Absent |
| Plant size | Medium |
| Head shape | Non-heading |
| Butt Shape | Rounded |
| Midrib | Moderately raised |

In one aspect the invention provides a new type of lettuce (*Lactuca sativa*) variety, designated 79-941 RZ. Lettuce cultivar 79-941 RZ exhibits a combination of traits including resistance to downy mildew (*Bremia lactucae*) races B1:16EU to B1:36EU and B1:1US to B1:9US, resistance to currant-lettuce aphid (*Nasonovia ribisnigri*) biotype Nr:0, and resistance to Lettuce Mosaic Virus (LMV) race LMV:1, as well as having a reduced wound induced surface discoloration and a medium plant size.

In an embodiment, the invention relates to lettuce plants that have all the physiological and morphological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that may be introduced by backcrossing, useful traits may be introduced directly into the plant of the invention, being a plant of lettuce variety 79-941 RZ, by genetic transformation techniques; and, such plants of lettuce variety 79-941 RZ that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, being a plant of lettuce variety 79-941 RZ or may, alternatively, be used for the preparation of transgenes which may be introduced by backcrossing. Methods for the transformation of plants, including lettuce, are well known to those of skill in the art.

Vectors used for the transformation of lettuce cells are not limited so long as the vector may express an inserted DNA in the cells. For example, vectors which may comprise promoters for constitutive gene expression in lettuce cells (e.g., cauliflower mosaic virus 35S promoter) and promoters inducible by exogenous stimuli may be used. Examples of suitable vectors include pBI binary vector. The "lettuce cell" into which the vector is to be introduced includes various forms of lettuce cells, such as cultured cell suspensions, protoplasts, leaf sections, and callus. A vector may be introduced into lettuce cells by known methods, such as the polyethylene glycol method, polycation method, electroporation, Agrobacterium-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those which may be comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target lettuce cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of lettuce variety 79-941 RZ.

Agrobacterium-mediated transfer is another widely applicable system for introducing gene loci into plant cells. An advantage of the technique is that DNA may be introduced into whole plant tissues, thereby bypassing the need for regeneration of an intact plant from a protoplast. Agrobacterium transformation vectors are capable of replication in E. coli as well as Agrobacterium, allowing for convenient manipulations. Moreover, advances in vectors for Agrobacterium-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, Agrobacterium containing both armed and disarmed Ti genes may be used for transformation. In those plant strains where Agrobacterium-mediated transformation is efficient, it is the method of choice because of the facile and defined nature of the gene locus transfer. The use of Agrobacterium-mediated plant integrating vectors to introduce DNA into plant cells, including lettuce plant cells, is well known in the art (See, e.g., U.S. Pat. Nos. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for lettuce plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins (psaD, psaF, psaE, PC, FNR, atpC, atpD, cab, rbcS) (see U.S. Pat. No. 7,161,061), the CAB-1 promoter (see U.S. Pat No. 7,663,027), the promoter from maize prolamin seed storage protein (see U.S. Pat No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the lettuce variety of this invention include, for example, DNA sequences or genes from another species, or even genes or sequences which originate with or are present in lettuce species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of lettuce variety 79-941 RZ. Non-limiting examples of particular genes and corresponding phenotypes one may choose to introduce into a lettuce plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat No. 7,576,262, "Modified gene-silencing RNA and uses thereof.")

U.S. Pats. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. Patents that may concern transformed lettuce and/or methods of transforming lettuce or lettuce plant cells, and techniques from these US Patents, as well as promoters, vectors, etc., may be employed in the practice of this invention to introduce exogenous nucleic acid sequence(s) into a plant of lettuce variety 79-941 RZ (or cells thereof), and exemplify some exogenous nucleic acid sequence(s) which may be introduced into a plant of lettuce variety 79-941 RZ (or cells thereof) of the invention, as well as techniques, promoters, vectors etc., to thereby obtain further plants of lettuce variety 79-941 RZ, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems. (See generally U.S. Pat No. 7,041,876 on lettuce being recognized as a plant that may be regenerated from cultured cells or tissue).

Also, the invention comprehends methods for producing a seed of a "79-941 RZ"-derived lettuce plant which may comprise (a) crossing a plant of lettuce variety 79-941 RZ, a sample of seed of which having been deposited under NCIMB Accession No. 43672, with a second lettuce plant, and (b) whereby seed of a 79-941 RZ-derived lettuce plant form. Such a method may further comprise (c) crossing a plant grown from 79-941 RZ-derived lettuce seed with itself or with a second lettuce plant to yield additional 79-941 RZ-derived lettuce seed, (d) growing the additional 79-941 RZ-derived lettuce seed of step (c) to yield additional 79-941 RZ-derived lettuce plants, and (e) repeating the crossing and growing of steps (c) and (d) for an additional 3-10 generations to further generate 79-941 RZ-derived lettuce plants.

The invention further relates to the above methods that may further comprise selecting at steps b), d), and e), a 79-941 RZ-derived lettuce plant, exhibiting one or more or all of the physiological and morphological characteristics of lettuce variety 79-941 RZ, a sample of seed of said variety having been deposited under NCIMB accession No. 43672, and other selected traits.

In particular, the invention relates to methods for producing a seed of a 79-941 RZ-derived lettuce plant which may comprise (a) crossing a plant of lettuce variety 79-941 RZ, a sample of seed of which having been deposited under NCIMB Accession No. 43672, with a second lettuce plant and (b) whereby seed of a 79-941 RZ-derived lettuce plant forms, wherein such a method may further comprise (c) crossing a plant grown from 79-941 RZ-derived lettuce seed with itself or with a second lettuce plant to yield additional 79-941 RZ-derived lettuce seed, (d) growing the additional 79-941 RZ-derived lettuce seed of step (c) to yield additional 79-941 RZ-derived lettuce plants and selecting plants exhibiting one or more or all of the physiological and morphological characteristics of lettuce variety 79-941 RZ , and (e) repeating the crossing and growing of steps (c) and (d) for an additional 3-10 generations to further generate 79-941 RZ-derived lettuce plants that exhibit one or more or all of the physiological and morphological characteristics of lettuce variety 79-941 RZ.

The invention additionally provides a method of introducing at least one new trait into a plant of lettuce variety 79-941 RZ which may comprise: (a) crossing a plant of lettuce variety 79-941 RZ, a sample of seed of which having been deposited under NCIMB Accession No. 43672, with a second lettuce plant that may comprise at least one new trait to produce progeny seed; (b) harvesting and planting the progeny seed to produce at least one progeny plant of a subsequent generation, wherein the progeny plant may comprise the at least one new trait; (c) crossing the selected progeny plant with a plant of lettuce variety 79-941 RZ, to produce backcross progeny seed; (d) harvesting and planting the backcross progeny seed to produce a backcross progeny plant, (e) repeating steps (c) and (d) for at least three additional generations to produce backcross progeny that may comprise the at least one new trait and all of the physiological and morphological characteristics of a plant of lettuce variety 79-941 RZ, when grown in the same environmental conditions. The invention, of course, includes a lettuce plant produced by this method.

Backcrossing may also be used to improve an inbred plant. Backcrossing transfers a specific desirable trait from one inbred or non-inbred source to an inbred that lacks that trait. This may be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. When a plant of lettuce variety 79-941 RZ, a sample of seed of which having been deposited under NCIMB Accession No. 43672, is used in backcrossing, offspring retaining one or more or all of the physiological and morphological characteristics of lettuce variety 79-941 RZ are progeny within the ambit of the invention. Backcrossing methods may be used with the present invention to improve or introduce a characteristic into a plant of the invention, being a plant of lettuce variety 79-941 RZ. See, e.g., Pat. No. 7,705,206 (incorporated herein by reference consistent with the above INCORPORATION BY REFERENCE section), for a general discussion relating to backcrossing.

The invention further involves a method of determining the genotype of a plant of lettuce variety 79-941 RZ, a sample of seed of which has been deposited under NCIMB Accession No. 43672, or a first generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium. The plurality of polymorphisms is indicative of and/or gives rise to the expression of the physiological and morphological characteristics of lettuce variety 79-941 RZ.

There are various ways of obtaining genotype data from a nucleic acid sample. Genotype data may be gathered which is specific for certain phenotypic traits (e.g. gene sequences), but also patterns of random genetic variation may be obtained to construct a so-called DNA fingerprint. Depending on the technique used a fingerprint may be obtained that is unique for lettuce variety 79-941 RZ. Obtaining a unique DNA fingerprint depends on the genetic variation present in a variety and the sensitivity of the fingerprinting technique. A technique known in the art to provide a good fingerprint profile is called AFLP fingerprinting technique (See generally U.S. Pat No. 5,874,215), but there are many other marker based techniques, such as RFLP (or Restriction fragment length polymorphism), SSLP (or Simple sequence length polymorphism), RAPD (or Random amplification of polymorphic DNA) VNTR (or Variable number tandem repeat), Microsatellite polymorphism, SSR (or Simple sequence repeat), STR (or Short tandem repeat), SFP (or Single feature polymorphism) DArT (or Diversity Arrays Technology), RAD markers (or Restriction site associated DNA markers) (e.g. Baird et al. PloS One Vol. 3 e3376, 2008; Semagn et al. African Journal of Biotechnology Vol. 5 number 25 pp. 2540-2568, 29 December, 2006). Nowadays, sequence-based methods are utilizing Single Nucleotide Polymorphisms (SNPs) that are randomly distributed across genomes, as a common tool for genotyping (e.g. Elshire et al. PloS One Vol. 6: e19379, 2011; Poland et al. PloS One Vol. 7: e32253; Truong et al. PLoS One Vol. 7 number 5: e37565, 2012).

With any of the aforementioned genotyping techniques, polymorphisms may be detected when the genotype and/or sequence of the plant of interest is compared to the genotype and/or sequence of one or more reference plants. As used herein, the genotype and/or sequence of a reference plant may be derived from, but is not limited to, any one of the following: parental lines, closely related plant varieties or species, complete genome sequence of a related plant variety or species, or the de novo assembled genome sequence of one or more related plant varieties or species. For example, it is possible to detect polymorphisms for the characteristic of wound induced surface discoloration by comparing the genotype and/or the sequence of lettuce variety 79-941 RZ with the genotype and/or the sequence of one or more reference plants. The reference plant(s) used for comparison in this example may for example be, but is not limited to, the comparison variety Codex RZ.

The polymorphism revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

Lettuce leaves are sold in packaged form, including without limitation as pre-packaged lettuce salad or as lettuce heads. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the lettuce leaves of the invention. Thus, the invention comprehends the use of and methods for making and using the leaves of the lettuce plant of the invention, as well as leaves of lettuce plants derived from the invention. The invention further relates to a container which may comprise one or more plants of the invention, or one or more lettuce plants derived from a plant of the invention, in a growth substrate for harvest of leaves from the plant in a domestic environment. This way the consumer may pick very fresh leaves for use in salads. More generally, the invention includes one or more plants of the invention or one or more plants derived from lettuce of the invention, wherein the plant is in a ready-to-harvest condition, including with the consumer picking his own, and further including a container which may comprise one or more of these plants.

The invention is further described by the following numbered paragraphs:

1. A seed of lettuce variety 79-941 RZ, a sample of seed of said variety having been deposited under NCIMB accession No. 43672.
2. A lettuce plant grown from the seed of paragraph 1.
3. A lettuce plant, or a part thereof, having all the physiological and morphological characteristics of the lettuce plant of paragraph 2.
4. A part of the lettuce plant of paragraph 2, wherein said part comprises a microspore, pollen, ovary, ovule, embryo sac, egg cell, cutting, root, stem, cell or protoplast.
5. A tissue culture of regenerable cells or protoplasts from the lettuce plant of paragraph 2.
6. The tissue culture of paragraph 6, wherein said cells or protoplasts of the tissue culture are derived from a tissue comprising a leaf, pollen, embryo, cotyledon, hypocotyl, meristematic cell, root, root tip, anther, flower, seed or stem.
7. A lettuce plant regenerated from the tissue culture of paragraphs 5 or 6, wherein the regenerated plant expresses all of the physiological and morphological characteristics of lettuce variety 79-941 RZ, a sample of seed of said variety having been deposited under NCIMB accession No. 43672.
8. A method of vegetatively propagating a plant of lettuce variety 79-941 RZ comprising (a) collecting tissue capable of being propagated from a lettuce plant of paragraph 2, (b) cultivating the tissue to obtain proliferated shoots and rooting the proliferated shoots to obtain rooted plantlets, and (c) optionally growing plants from the rooted plantlets.
9. A method for producing a progeny plant of lettuce cultivar 79-941 RZ, comprising crossing a lettuce plant of paragraph 2 with itself or with another lettuce plant, harvesting the resultant seed, and growing said seed.
10. A progeny plant produced by the method of paragraph 9, wherein said progeny exhibits all the morphological and physiological characteristics of the lettuce variety designated 79-941 RZ, a sample of seed of said variety having been deposited under NCIMB accession No. 43672.
11. The progeny plant of paragraph 10, wherein said progeny plant is modified in one or more other characteristics.
12. A lettuce plant of paragraph 2 further comprising a transgene.
13. The plant of paragraph 12, wherein the transgene is introduced via transformation.
14. A method for producing a modified lettuce plant comprising mutagenizing the seed of paragraph 1 and growing said seed.
15. A method for producing a modified lettuce plant comprising mutagenizing the plant of any one of paragraphs 2, 3 or 7.
16. A method for producing a modified lettuce plant comprising mutagenizing the part of plant of any one of paragraphs 3 or 4.
17. A method for producing a modified lettuce plant comprising mutagenizing the tissue culture of any one of paragraphs 5 or 6.
18. A method of producing a lettuce seed comprising crossing a male parent lettuce plant with a female parent lettuce plant and harvesting the resultant lettuce seed, wherein said male parent lettuce plant or said female parent lettuce plant is the lettuce plant of paragraph 2.
19. An F1 lettuce seed produced by the method of paragraph 18.
20. A lettuce plant produced by growing the seed of paragraph 19.
21. A method for producing a seed of a 79-941 RZ-derived lettuce plant comprising (a) crossing a plant of lettuce variety 79-941 RZ, a sample of seed of which having been deposited under NCIMB Accession No. 43672, with a second lettuce plant, and (b) whereby seed of a 79-941 RZ-derived lettuce plant forms.
22. The method of paragraph 21 further comprising (c) crossing a plant grown from 79-941 RZ-derived lettuce seed with itself or with a second lettuce plant to yield additional 79-941 RZ-derived lettuce seed, (d) growing the additional 79-941 RZ-derived lettuce seed of step (c) to yield additional 79-941 RZ-derived lettuce plants, and (e) repeating the crossing and growing of steps (c) and (d) for an additional 3-10 generations to generate further 79-941 RZ-derived lettuce plants, and (f) whereby seed of a 79-941 RZ-derived lettuce plant forms.
23. A method of introducing at least one new trait into a plant of lettuce variety 79-941 RZ comprising: (a) crossing a plant of lettuce variety 79-941 RZ, a sample of seed of which having been deposited under NCIMB Accession No. 43672, with a second lettuce plant that comprises at least one new trait to produce progeny seed, (b) harvesting and planting the progeny seed to produce at least one progeny plant of a subsequent generation, wherein the progeny plant comprises the at least one new trait, (c) crossing the progeny plant with a plant of lettuce variety 79-941 RZ to produce backcross progeny seed, (d) harvesting and planting the backcross progeny seed to produce a backcross progeny plant, and (e) repeating steps (c) and (d) for at least three additional generations to produce a lettuce plant of variety 79-941 RZ comprising at least one new trait and all of the physiological and morphological characteristics of a plant of lettuce variety 79-941 RZ, when grown in the same environmental conditions.
24. The lettuce plant produced by the method of paragraph 23, wherein the plant comprises the at least one new trait and otherwise all of the physiological and morphological characteristics of a lettuce plant of lettuce variety 79-941 RZ.
25. A method for producing lettuce leaves as a food product comprising sowing the seed of paragraph 1 and growing the seed into a harvestable lettuce plant and harvesting the head or leaves of said plant, optionally processing and/or packaging the head or the leaves.
26. A container comprising one or more lettuce plants of paragraph 2 for harvest of leaves.

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A seed of lettuce variety 79-941 RZ, a sample of seed of said variety having been deposited under NCIMB Accession No. 43672.

2. A lettuce plant grown from the seed of claim 1.

3. A lettuce plant, or a part thereof, having all the physiological and morphological characteristics of the lettuce plant of claim 2.

4. A part of the lettuce plant of claim 2, wherein said part comprises a microspore, pollen, ovary, ovule, embryo sac, egg cell, cutting, root, stem, cell or protoplast.

5. A tissue culture of regenerable cells or protoplasts from the lettuce plant of claim 2.

6. A lettuce plant regenerated from the tissue culture of claim 5, wherein the regenerated plant expresses all of the physiological and morphological characteristics of lettuce variety 79-941 RZ, a sample of seed of said variety having been deposited under NCIMB Accession No. 43672.

7. A method of vegetatively propagating a plant of lettuce variety 79-941 RZ comprising
   (a) collecting tissue capable of being propagated from a lettuce plant of claim 2,
   (b) cultivating the tissue to obtain proliferated shoots and rooting the proliferated shoots to obtain rooted plantlets, and
   (c) optionally growing plants from the rooted plantlets.

8. A method for producing a progeny plant of lettuce variety 79-941 RZ, a sample of seed of said variety having been deposited under NCIMB Accession No. 43672, comprising
   crossing a lettuce plant of claim 2 with itself or with another lettuce plant,
   harvesting the resultant seed, and
   growing said seed.

9. A progeny plant produced by the method of claim 8, wherein said progeny plant exhibits all the morphological and physiological characteristics of the lettuce variety designated 79-941 RZ, a sample of seed of said variety having been deposited under NCIMB Accession No. 43672.

10. A lettuce plant of lettuce variety 79-941 RZ, a sample of seed of said variety having been deposited under NCIMB Accession No. 43672, said plant further comprising a transgene.

11. The plant as claimed in claim 10, wherein the transgene is introduced via transformation.

12. A method for producing a modified lettuce plant comprising mutagenizing the seed of claim 1 and growing said seed.

13. A method for producing a modified lettuce plant comprising mutagenizing the plant of any one of claims 2, 3 or 6.

14. A method for producing a modified lettuce plant comprising mutagenizing the part of plant of any one of claims 3 or 4.

15. A method for producing a modified lettuce plant comprising mutagenizing the tissue culture of claim 5.

16. A method of producing a lettuce seed comprising
   crossing a male parent lettuce plant with a female parent lettuce plant and
   harvesting the resultant lettuce seed,
   wherein said male parent lettuce plant or said female parent lettuce plant is the lettuce plant of claim 2.

17. An F1 lettuce seed produced by the method of claim 16.

18. A lettuce plant produced by growing the seed of claim 17.

19. A method for producing a seed of a 79-941 RZ-derived lettuce plant comprising
   (a) crossing a plant of lettuce variety 79-941 RZ, a sample of seed of which having been deposited under NCIMB Accession No. 43672, with a second lettuce plant, and
   (b) whereby seed of a 79-941 RZ-derived lettuce plant forms.

20. The method of claim 19 further comprising
   (c) crossing a plant grown from 79-941 RZ-derived lettuce seed with itself or with a second lettuce plant to yield additional 79-941 RZ-derived lettuce seed,
   (d) growing the additional 79-941 RZ-derived lettuce seed of step (c) to yield additional 79-941 RZ-derived lettuce plants, and
   (e) repeating the crossing and growing of steps (c) and (d) for an additional 3-10 generations to generate further 79-941 RZ-derived lettuce plants, and
   (f) whereby seed of a 79-941 RZ-derived lettuce plant forms.

21. A method of introducing at least one new trait into a plant as claimed in claim 2 comprising:
   (a) crossing a plant of lettuce variety 79-941 RZ, a sample of seed of which having been deposited under NCIMB Accession No. 43672, with a second lettuce plant that comprises at least one new trait to produce progeny seed,
   (b) harvesting and planting the progeny seed to produce at least one progeny plant of a subsequent generation, wherein the progeny plant comprises the at least one new trait,
   (c) crossing the progeny plant with a plant of lettuce variety 79-941 RZ to produce backcross progeny seed,
   (d) harvesting and planting the backcross progeny seed to produce a backcross progeny plant, and
   (e) repeating steps (c) and (d) for at least three additional generations to produce a lettuce plant of variety 79-941 RZ comprising at least one new trait and all of the physiological and morphological characteristics of a plant of lettuce variety 79-941 RZ, when grown in the same environmental conditions.

22. A method for producing lettuce leaves as a food product comprising
   sowing the seed of claim 1,
   growing the seed into a harvestable lettuce plant and harvesting the head or leaves of said plant,
   optionally processing and/or packaging the head or the leaves.

23. A container comprising one or more lettuce plants of claim 2 for harvest of leaves.

24. The lettuce plant of claim 2, which is a plant grown from seed having been deposited under NCIMB Accession No. 43672.

* * * * *